United States Patent
Pagan

(10) Patent No.: US 7,077,135 B2
(45) Date of Patent: Jul. 18, 2006

(54) RESUSCITATORS, PARTS AND ASSEMBLIES

(75) Inventor: Eric Pagan, Hythe (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 10/901,050

(22) Filed: Jul. 29, 2004

(65) Prior Publication Data

US 2005/0039751 A1 Feb. 24, 2005

(30) Foreign Application Priority Data

Aug. 22, 2003 (GB) ................................ 0319743.1

(51) Int. Cl.
*A62B 7/00* (2006.01)
*A62B 9/00* (2006.01)

(52) U.S. Cl. .................... 128/205.23; 128/205.13; 128/205.14; 128/205.15; 128/205.17; 128/203.28

(58) Field of Classification Search .......... 128/205.23, 128/204.28, 205.13, 203.28, 205.17, 204.18, 128/205.24; 116/200, 201, 206, 209
See application file for complete search history.

(56) References Cited

U.S. PATENT DOCUMENTS

| | | | | |
|---|---|---|---|---|
| 4,945,918 A | * | 8/1990 | Abernathy | .............. 600/532 |
| 5,357,951 A | * | 10/1994 | Ratner | ................... 128/205.24 |
| 5,375,592 A | * | 12/1994 | Kirk et al. | ............. 128/207.14 |
| 5,456,249 A | * | 10/1995 | Kirk | ...................... 128/205.13 |
| 5,517,985 A | * | 5/1996 | Kirk et al. | ............. 128/205.28 |
| 5,606,131 A | * | 2/1997 | Pope | ........................... 73/744 |
| 5,679,884 A | * | 10/1997 | Kirk | ........................... 73/23.3 |
| 5,749,358 A | * | 5/1998 | Good et al. | ............ 128/205.23 |
| 6,058,933 A | * | 5/2000 | Good et al. | ............ 128/205.13 |
| 6,123,075 A | * | 9/2000 | Kirk | ..................... 128/205.13 |
| 6,427,687 B1 | * | 8/2002 | Kirk | ..................... 128/203.11 |
| 6,502,573 B1 | | 1/2003 | Ratner | |
| 6,539,941 B1 | * | 4/2003 | Haubeil | ................. 128/205.13 |

FOREIGN PATENT DOCUMENTS

GB 2218515 11/1989

* cited by examiner

*Primary Examiner*—Henry Bennett
*Assistant Examiner*—Nihir Patel
(74) *Attorney, Agent, or Firm*—Louis Woo

(57) ABSTRACT

A squeeze bag resuscitator has a flow diverter push fitted onto its exhaust outlet in any desired orientation. The diverter has a color change carbon dioxide indicator strip fixed to the inside surface of a transparent deflector plate. The indicator is protected from light externally by an opaque elastomeric strip attached by engaging surface formations to the outside of the plate. The indicator is also protected on the interior of the plate by an opaque strip, which projects from the diverter so that it can be removed by pulling on the free end.

20 Claims, 4 Drawing Sheets

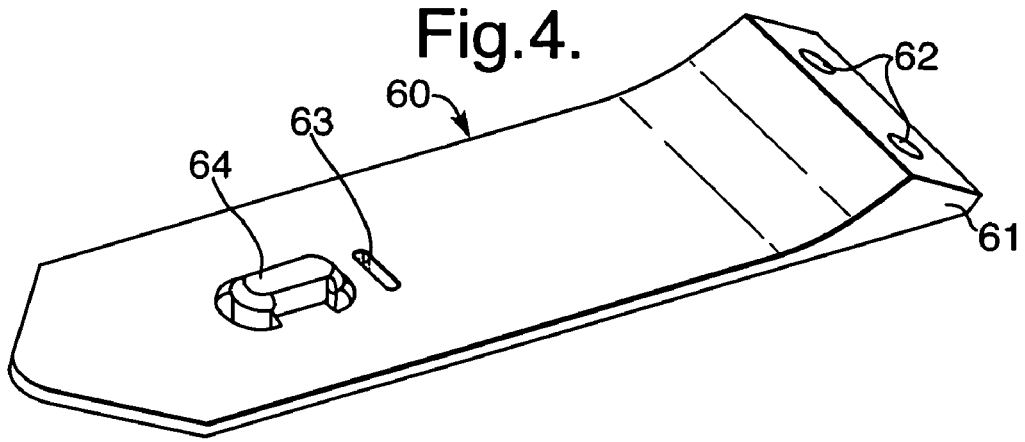
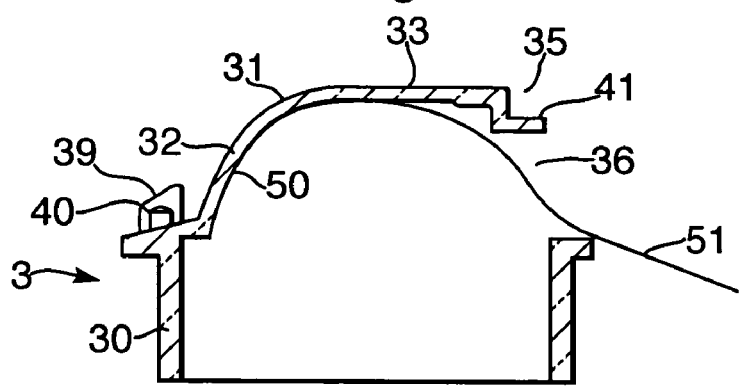
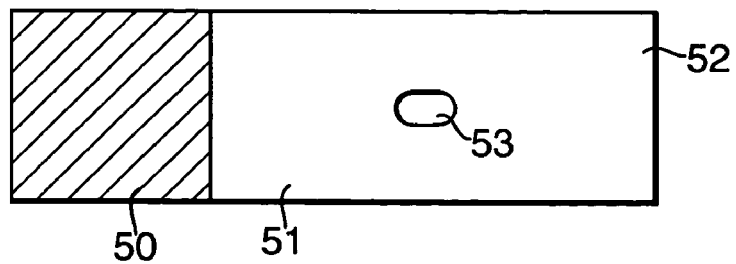

RESUSCITATORS, PARTS AND ASSEMBLIES

BACKGROUND OF THE INVENTION

This invention relates to resuscitators, parts and assemblies.

Resuscitators are used to ventilate a patient who is not breathing voluntarily. One type of resuscitator has a resilient squeeze bag that is squeezed by hand to administer air to a patient via a face mask, an endotracheal tube, laryngeal mask or the like. The resuscitator has a valve arrangement that directs air to a patient outlet coupling when the bag is squeezed and allows exhaled gas from the patient to flow directly to an exhaust outlet. The valve arrangement also allows air back in to refill the bag when it is released after having been squeezed. Where the resuscitator is used with an endotracheal tube it is important that checks are made to ensure that the tube is correctly placed, that is, to ensure it is in the trachea and not in the oesophagus. One way in which this can be done is by means of a carbon dioxide indicator since carbon dioxide is produced as a result of respiration and the level of this gas from the lungs significantly exceeds that in atmospheric air and in gas from the oesophagus. Hence, a low level of carbon dioxide is indicative of incorrect intubation. Carbon dioxide levels can be monitored in a well-equipped hospital with a capnograph. Alternatively, an indicator formed from a calorimetric substance could be used, usually in the form of a treated paper strip. The indicator can be connected directly to the endotracheal tube or, as proposed in U.S. Pat. No. 4,790,327, it can be incorporated into the exhaust outlet of the resuscitator. Resuscitators of this kind are sold by Nellcor of California, USA under the name Indgo. It is desirable for such indicators to be highly visible and reliable in their response. Other patents describing carbon dioxide indicators used with resuscitators include U.S. Pat. No. 5,749,358 and U.S. Pat. No. 6,058,933.

Alternative resuscitators have a source of air or oxygen, such as from a compressed gas cylinder, connected to a mechanical valve and regulator arrangement by which the user can supply gas to the patient. An example of such a resuscitator is described in GB 2282542. It is also desirable with this form of resuscitator, where it is connected to an endotracheal tube to be able to check that the tube has been correctly positioned in the trachea. It can also be desirable to check that the patient is breathing correctly when a resuscitator is used with a face mask or a laryngeal mask.

BRIEF SUMMARY OF THE INVENTION

It is an object of the present invention to provide an alternative resuscitator, part of a resuscitator and an assembly According to one aspect of the present invention there is provided a resuscitator having means for providing ventilation gas for a patient, a patient outlet for supplying the gas to the patient, an exhaust outlet for supplying exhaled gas from the patient to atmosphere, a diverter fitted on the exhaust outlet, the diverter including a diverter member inclined at an angle to the axis of the exhaust outlet, and an opening towards an end of the diverter member such that exhaled gas flowing through the exhaust outlet flows along an inner surface of the diverter member and out of the opening, the resuscitator including a colour-change carbon dioxide indicator mounted on the inner surface of the diverter member where it is exposed to flow through the diverter, and the indicator being visible externally of the diverter.

The diverter is preferably adjustable in orientation relative to the exhaust outlet and is preferably removable from the exhaust outlet. The diverter may be a push fit on the exhaust outlet. The diverter member is preferably of a transparent material. The resuscitator may include removable opaque means for protecting the indicator from light. The opaque means may include a removable strip of opaque material covering the exposed surface of the indicator internally of the deflector and the removable strip may have an end projecting beyond the opening of the diverter and may be arranged so that it can be removed by pulling on the end. The opaque means may include a strip of opaque material removably attached with and extending over an external surface of the diverter member. The external strip may be of an elastomeric material and may be attached with the diverter by means of engaging formations on the strip and the diverter. The resuscitator may include a squeeze bag of resilient material. The resuscitator may include a valve assembly having a tubular member extending within an outer housing and communicating with the patient outlet at one end and engaging a flexible diaphragm member at its other end by means of which flow of gas to the patient outlet and to the exhaust outlet is controlled, the tubular member being rotatable relative to the outer housing, and the tubular member being provided with a plurality of formations around its circumference arranged to allow a small amount of ventilation gas for supply to the patient via the tubular member to flow directly to the diverter regardless of the orientation of the tubular member.

According to another aspect of the present invention there is provided a diverter for a resuscitator according to the above one aspect of the invention.

According to a third aspect of the present invention there is provided an assembly of an endotracheal tube and a resuscitator according to the above one aspect of the invention with its patient outlet coupled with a machine end of the endotracheal tube.

An assembly of a squeeze-bag resuscitator, endotracheal tube and flow diverter, according to the present invention, will now be described, by way of example, with reference to the accompanying drawing.

BRIEF DESCRIPTION OF THE DRAWINGS

FIG. 4 is a perspective view of the underside of the light-protecting strip;

FIG. 5 is a sectional side-elevation view of the flow diverter without the light-protecting strip;

FIG. 6 is a plan view of the indicator used in the diverter;

DETAILED DESCRIPTION OF THE PREFERRED EMBODIMENTS

Figure 1:
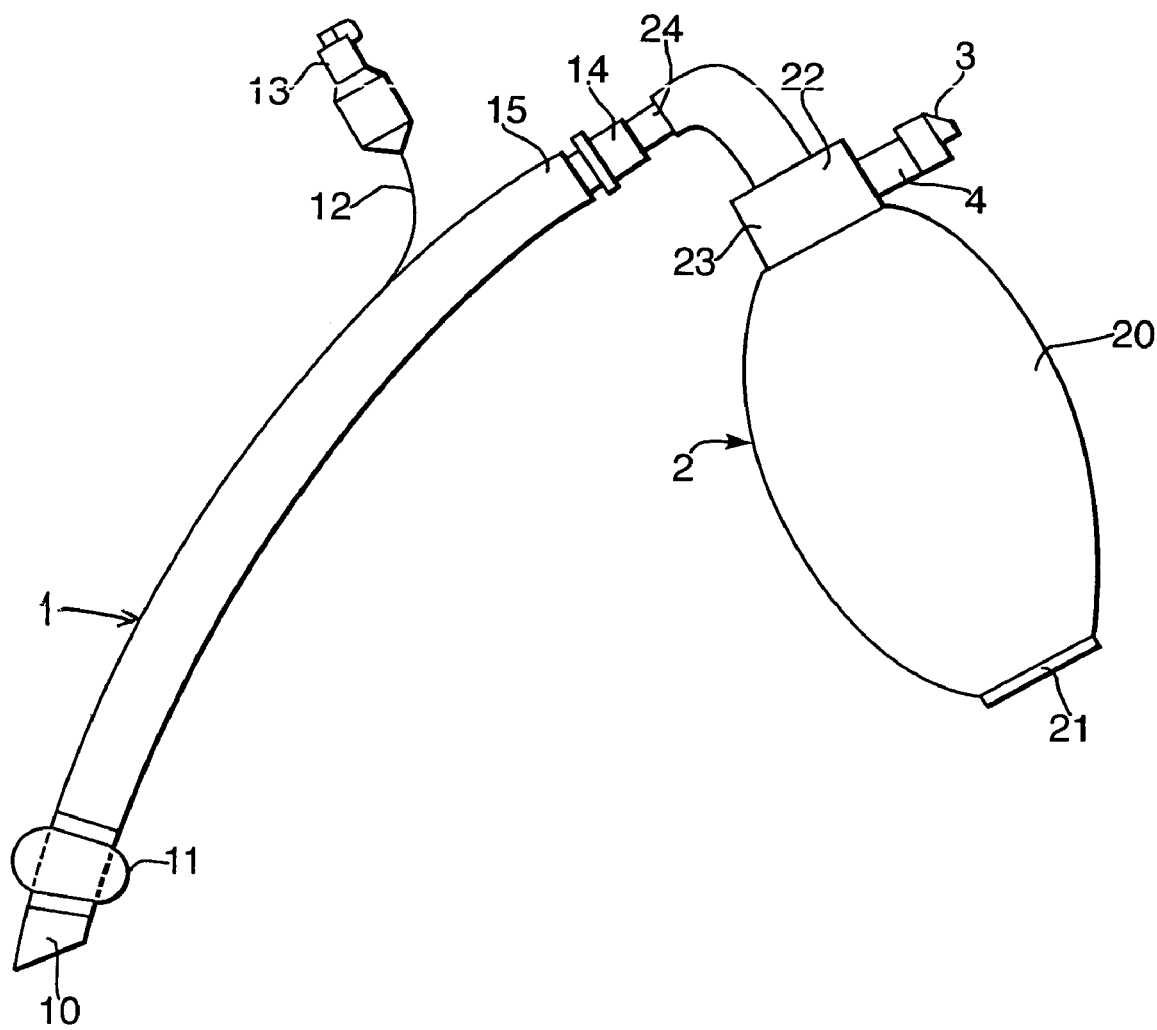
FIG. 1 is a side elevation view of the assembly.

With reference first to FIG. 1, the assembly includes a conventional endotracheal tube 1, a squeeze-bag resuscitator 2 connected to the machine end of the tube and a flow diverter 3 connected on the exhaust outlet 4 of the resuscitator.

The patient end 10 of the endotracheal tube 1 is intended for placement in the trachea and has a cuff 11 towards its patient end that is inflatable via an inflation line 12 and connector 13, so that it seals with the trachea. A connector 14 is fitted in the machine end 15 of the tube 1.

The resuscitator 2 has a bulb-shape squeeze bag 20 of a resilient plastics material selected so that the bag can be squeezed by hand and recovers its original shape when released. At its lower end the resuscitator 2 has a one-way inlet valve 21 that allows air into the bag 20 when this is recovering its original shape but prevents flow of air out of the bag through the valve when the bag is squeezed. At its upper end the resuscitator 2 has a valve assembly 22, which may be of the kind described in U.S. Pat. No. 4,774,941. The valve assembly 22 has a housing 23 of tubular shape in which the valve mechanism is housed and which is bonded at its lower end to the bag 20. The upper end of the housing 23 has a lateral extension 24 projecting to one side, which provides a patient outlet. The patient outlet 24 is coupled to the connector 14 fitted into the endotracheal tube 1. The exhaust outlet 4 projects laterally close to the lower end of the housing 23 in the form of a short, externally-tapered tubular port of circular cross section and 30 mm diameter. Inside the housing 23 the valve assembly 22 includes a conventional valve mechanism that opens the passage between the inside of the bag 20 and the patient outlet 24 when the bag is squeezed but blocks flow to the exhaust outlet 4. When the bag 20 is released the valve mechanism prevents flow back into the bag but allows exhaled air from the patient to flow to the exhaust outlet 4.

Figure 2:
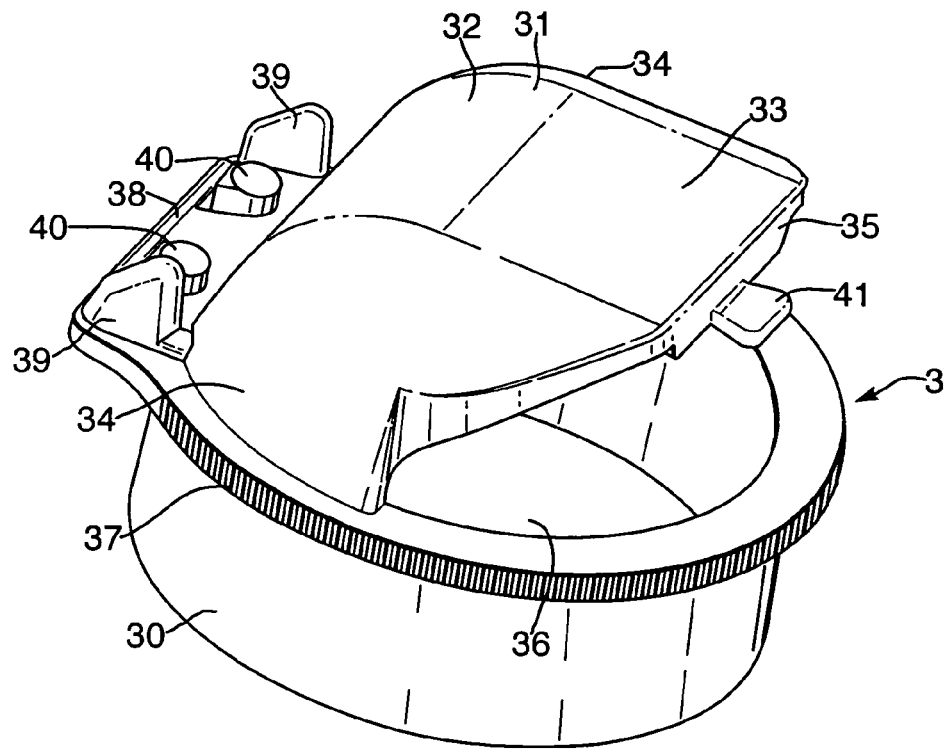
FIG. 2 is a perspective view of the flow diverter to a greater scale without its light-protecting strip.
Figure 3:
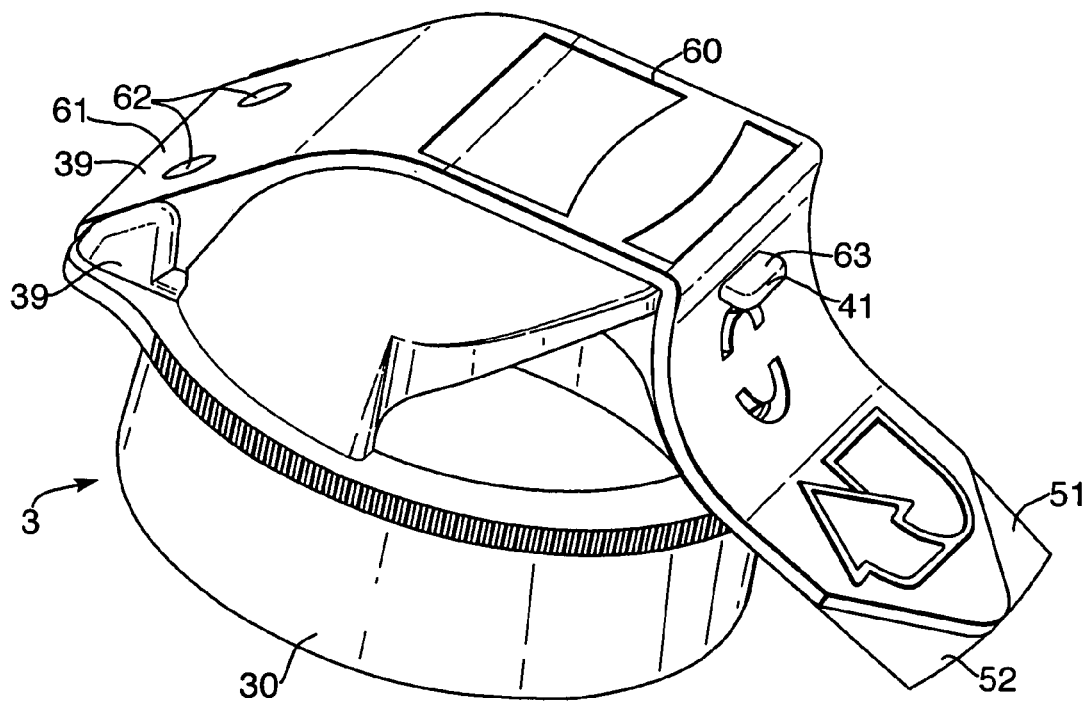
FIG. 3 is a perspective view of the flow diverter with its light-protecting strip.

The flow diverter or deflector 3 is shown in greater detail in FIGS. 2, 3 and 5. The deflector 3 is moulded of a transparent plastics material and has a main tubular portion 30 of circular section with a slight internal taper that is a push fit on the outside of the exhaust outlet 4. A diverter member in the form of a deflector plate 31 extends from the upper end of the tubular portion 30 to one side. The plate 31 is curved at one end 32 where it joins with the main portion 30, its other end 33 being straight and extending transversely of the main portion. The plate has curved side portions 34, which join with the upper end of the main portion 30. The plate 31 extends laterally across the major part of the width of the main portion 30 its right-hand, free end 35 being spaced forwardly of the end of the tubular portion 30 to provide an opening 36 of substantially segment shape extending across about half the width of the main portion. The diverter 3 also has knurled flange 37 extending around its upper end, which is enlarged towards the closed side of the diverter to form a small platform 38. The platform 38 carries two locating fingers 39 of triangular shape at opposite ends and two upwardly-projecting pegs 40 adjacent respective ones of the locating fingers. The diverter 3 further has a small tongue 41 projecting forwardly from the free end 35 of the plate 31.

The flow deflector 3 is used to divert the flow of exhaust gas away from the user. The need for this arises because, in the case of trauma, the exhaust gas may include aerosol dispersion of blood or other body fluids, which can present a hazard to the user. The user can fit the deflector 3 on the exhaust outlet 4 at any desired orientation. If he needs to change the position of the resuscitator 2 he can readily twist the deflector 3 around to a new position at which gas emerging from the outlet 4 is directed away from him.

The deflector 3 also includes a colour-change carbon dioxide indicator 50 (FIG. 6) in the form of a small square sheet of chemically treated material that changes color when exposed to gas containing carbon dioxide above a certain level. These kinds of indicator are sold by Bregas AB of Sweden. In particular, the indicator 50 has one color when exposed to normal atmospheric air and changes to a different colour when exposed to exhaled air containing elevated levels of carbon dioxide. The speed of response of the indicator 50 is sufficiently rapid that the indicator will change colour backwards and forwards between breaths. The indicator 50 is adhered to the inside surface of the curved part 32 of the deflector plate 31 so that it is exposed, directly in line with emerging gas flowing through the tubular portion 30, which impinges on the exposed surface of the indicator. This ensures that the indicator 50 responds rapidly to changes in composition of the gas. Because the indicator 50 is mounted close to the end of the deflector and because the plate 31 is exposed around its end and sides, the indicator is exposed freely to atmospheric air, thereby ensuring that, when the flow of respiration gas ceases, it is quickly exposed to the atmospheric air to ensure a rapid change back to its low-carbon dioxide colour.

Before use, the indicator 50 is protected by a rectangular peel-off strip 51 attached with the indicator internally of the deflector and having a free end 52 projecting beyond the end 35 of the deflector plate 31 to provide a tab by which the strip can be gripped and pulled off the indicator, leaving the indicator in place. The peel-off strip 51 also has an oval hole 53 located about half way between its free end and the indicator 50. The transparent nature of the deflector plate 31 enables the indicator 50 to be viewed through the plate so that its colour change is readily visible externally. Because the deflector 3 is oriented with its opening 36 away from the user, the indicator 40 is automatically oriented to face towards the user. The angle and curve of the deflector plate 31 further increase the range of angles over which the indicator is visible. Incorporating the indicator 50 in the flow deflector 3 ensures that there is no risk of the deflector obscuring an indicator such as might happen if the indicator were placed in the exhaust outlet itself.

Some colour-change indicators are sensitive to light and have to be protected during storage. In the present invention this is achieved by making the peel-off strip 51 covering the exposed surface of the indicator from an opaque material and by placing an additional, opaque, light-protecting strip 60 on the outside of the deflector plate 31. The protecting strip 60 is shown in FIGS. 3 and 4 and comprises a moulded strip of a flexible, opaque, elastomeric material. One end 61 of the strip 60 is thickened with a portion of triangular section and has two retaining apertures 62 through its thickness. The width of the strip 60 is such that it is a close fit between the two locating fingers 39 on the deflector with the pegs 40 extending in the retaining apertures 62. The pegs 40 are slightly larger than the apertures 62 so that the strip has to be deformed slightly to accommodate the pegs and provides a secure retention of the strip. The strip 60 also has a small rectangular aperture 63 at a location about two thirds the way along its length from its thickened end and located to receive the tongue 41 so that the strip is held down across the plate 31 when the tongue is engaged in the aperture. The underside of the strip 60 also has a hooked projection 64 of oval shape located just forwardly of aperture 63. The projection 64 is located to align with the hole 53 in the indicator peel-off strip 51 where this projects beyond the end 35 of the deflector plate. The projection 64 is slightly larger than the hole 53 so that it grips the peel-off strip 51 securely when pushed through the hole.

In this configuration, as shown in FIG. 3, the protecting strip 60 extends downwardly and forwardly beyond the free end 35 of the deflector plate 31 and is attached with the indicator peel-off strip 51. The indicator 50 is protected from light during storage by the peel-off strip 51 on one side and by the protecting strip 60 on the other side.

To use, the free end of the protecting strip 60 is gripped and pulled up so that it pulls away from the tongue 41 and then from the pegs 40. As it comes away, it pulls the peel-off strip 51 away from the indicator 50, thereby exposing it to gas flow through the deflector 30.

There are other ways in which the indicator could be protected from light. For example, an opaque dust cap could be fitted over the deflector before use to restrict the amount of light to which it was exposed.

Figure 7:
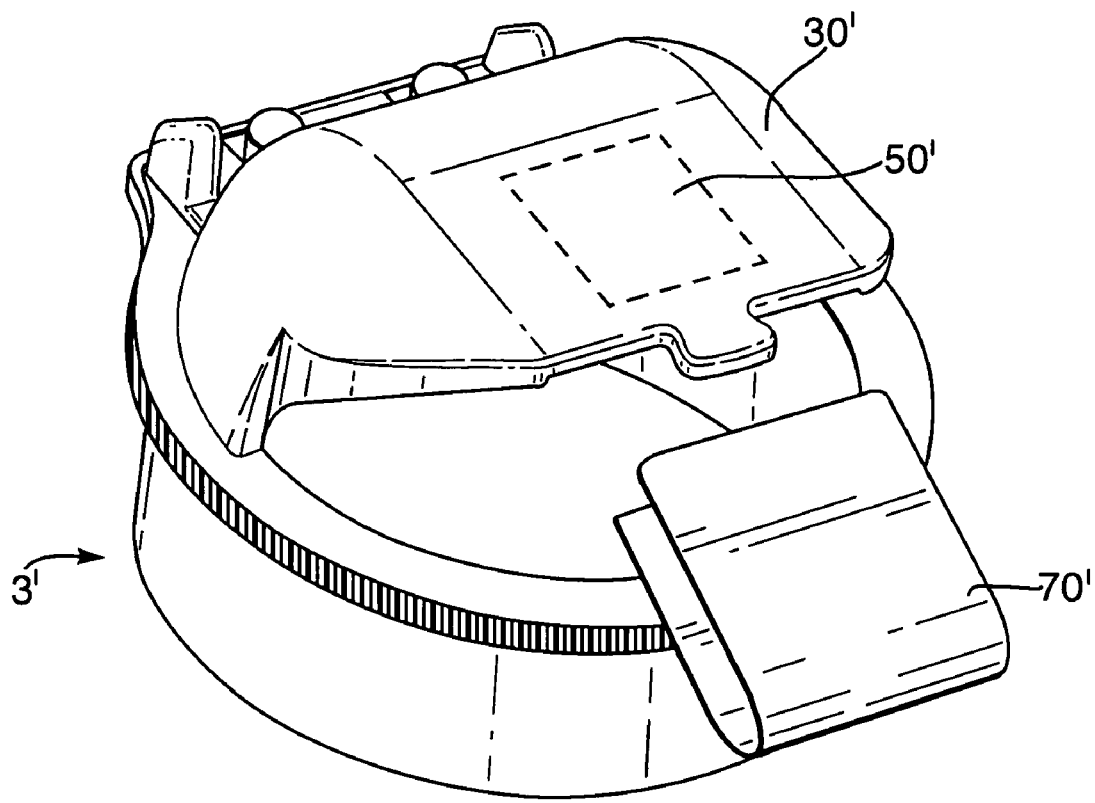
FIG. 7 is a perspective view of an alternative diverter.

As shown in FIG. 7, the indicator 50' could be located closer to the free end of the deflector plate 31' and be protected from light by an opaque U-section clip 70' shaped to fit over the free end of the deflector plate to cover the indicator on both sides. The clip 70' is retained in place on the diverter 3' by its resilience.

Figure 8:
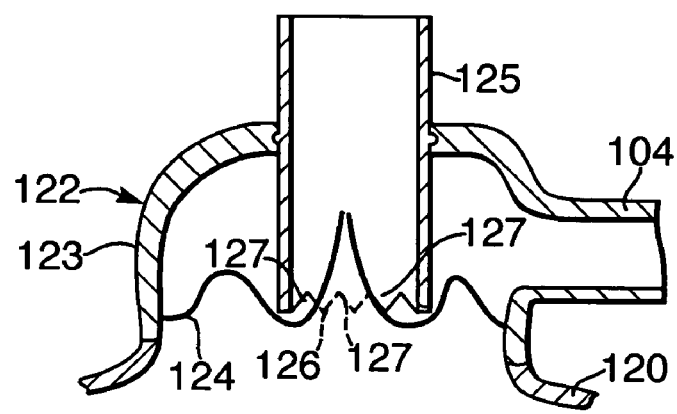
FIG. 8 is a sectional side elevation view of a part of a modified resuscitator.

The response of the indicator to changes in carbon dioxide levels between inhaled and exhaled gas can be improved by allowing a small flow of fresh air into the resuscitator exhaust outlet to help flush out exhaled air containing elevated levels of carbon dioxide. This is preferably achieved in the manner shown in FIG. 8 by modifying the resuscitator valve arrangement 122 to provide a small passage for air to flow from the interior of the squeeze bag 120 to the exhaust outlet 104. Where the valve arrangement 122 has a flexible diaphragm valve 124 that engages the lower end of an inner tube 125 providing the patient outlet of the resuscitator, this may be done simply by forming a small hole through the inner tube in alignment with the exhaust outlet 104. Alternatively, as shown in FIG. 8, the lower end 126 of the inner tube 125 may be provided with a formation, such as a V-shape groove 127 or other notch aligned with the exhaust outlet 104, which allows some of the fresh air supplied to the inner tube 125 by the squeeze bag 120 to escape to the exhaust outlet 104 and flush out any residual exhaled air having elevated levels of carbon dioxide. Where the inner tube 125 is rotatable relative to the valve housing 123, it preferably has several grooves 127 or similar formations around its circumference, as shown in FIG. 8, so that at least one of these is substantially aligned with the exhaust outlet 104 regardless of the orientation of the inner tube.

The deflector is not confined to use with squeeze bag resuscitators but could be used with other resuscitators having an exhaust outlet.

I claim:

1. A resuscitator for providing ventilation gas for a patient, said resuscitator comprising: a patient outlet for supplying said gas to the patient; an exhaust outlet for supplying exhaled gas from the patient to atmosphere; and a diverter fitted on said exhaust outlet, said diverter including a tubular portion, a diverter plate extending laterally from said tubular portion inclined at an angle to an axis of said tubular portion, and an opening between said plate and said tubular portion such that exhaled gas flowing through said exhaust outlet flows along an inner surface of said diverter plate and is diverted laterally out of said opening, wherein said diverter includes a color-change carbon dioxide indicator mounted on an inner surface of said diverter plate where it is exposed to flow through said diverter, and wherein said indicator is visible externally of said diverter.

2. A resuscitator according to claim 1, wherein said diverter is adjustable in orientation relative to said exhaust outlet.

3. A resuscitator according to claim 1, wherein said diverter is removable from said exhaust outlet.

4. A resuscitator according to claim 1, wherein the diverter is a push fit on the exhaust outlet.

5. A resuscitator according to claim 1, wherein said diverter plate is of a transparent material.

6. A resuscitator according to claim 1 including a removable opaque protector for protecting the indicator from light.

7. A resuscitator according to claim 6, wherein said opaque protector includes a removable strip of opaque material covering an exposed surface of said indicator internally of said deflector.

8. A resuscitator according to claim 7, wherein said removable strip has an end projecting beyond said opening of said diverter and is arranged so that it can be removed by pulling on said end.

9. A resuscitator according to claim 6, wherein said opaque protector includes a strip of opaque material removably attached with and extending over an external surface of said diverter plate.

10. A resuscitator according to claim 9, wherein said external strip is of an elastomeric material and is attached with said diverter by engaging formations on said strip and said diverter.

11. A resuscitator according to claim 1 including a squeeze bag of resilient material.

12. A resuscitator according to claim 1 including a valve assembly having an outer housing, a flexible diaphragm and a tubular member extending within said outer housing and communicating with said patient outlet at one end, said tubular member engaging said flexible diaphragm member at its other end by means of which flow of gas to said patient outlet and to said exhaust outlet is controlled, wherein said tubular member is rotatable relative to said outer housing, and wherein said tubular member is provided with a plurality of formations around its circumference arranged to allow a small amount of ventilation gas for supply to the patient via said tubular member to flow directly to said diverter regardless of the orientation of said tubular member.

13. A diverter for fitting on an exhaust outlet of a resuscitator, said diverter comprising a tubular portion shaped to fit on said exhaust outlet; a diverter plate extending laterally from said tubular portion inclined at an angle to said tubular portion; an opening between said plate and said tubular portion such that exhaled gas flowing through said exhaust outlet flows along an inner surface of said diverter plate and is diverted laterally and out of said opening; and a color-change carbon dioxide indicator mounted on an inner surface of said diverter plate where it is exposed to flow through said diverter, and wherein said indicator is visible externally of said diverter.

14. A diverter according to claim 13, wherein said diverter plate is of a transparent material and said indicator is visible externally through said diverter plate.

15. A diverter according to claim 13 including a removable opaque protector for protecting the indicator from light.

16. A diverter according to claim 15, wherein said opaque protector includes a removable strip of opaque material covering an exposed surface of said indicator internally of said deflector.

17. A diverter according to claim 16, wherein said removable strip has an end projecting beyond said opening of said diverter and is arranged so that it can be removed by pulling on said end.

18. A diverter according to claim 15, wherein said opaque protector includes a strip of opaque material removably attached with and extending over an external surface of said diverter plate.

19. A diverter according to claim 18, wherein said external strip is of an elastomeric material and is attached with said diverter by engaging formations on said strip and said diverter.

20. An assembly of an endotracheal tube and a resuscitator for providing ventilation gas for a patient via said tube, said resuscitator comprising: a patient outlet connected with said endotracheal tube; an exhaust outlet for supplying exhaled gas from said tube to atmosphere; and a diverter fitted on said exhaust outlet, said diverter including a tubular portion, a diverter plate extending laterally from said tubular portion inclined at an angle to an axis of said tubular portion, and an opening between said plate and said tubular portion such that exhaled gas flowing through said exhaust outlet flows along an inner surface of said diverter plate and out of said opening, wherein said diverter includes a color-change carbon dioxide indicator mounted on an inner surface of said diverter plate where it is exposed to flow through said diverter, and wherein said indicator is visible externally of said diverter.

* * * * *